US00PP23193P3

(12) United States Plant Patent
Sekiya

(10) Patent No.: US PP23,193 P3
(45) Date of Patent: Nov. 20, 2012

(54) PINEAPPLE PLANT NAMED 'FRANKLYNN'

(50) Latin Name: *Ananas comosus*
Varietal Denomination: Franklynn

(75) Inventor: Frank F Sekiya, Waimanalo, HI (US)

(73) Assignee: Frankie's Nursery LLC, Waimanalo, HI (US)

( * ) Notice: Subject to any disclaimer, the term of this patent is extended or adjusted under 35 U.S.C. 154(b) by 406 days.

(21) Appl. No.: 12/802,226

(22) Filed: Jun. 1, 2010

(65) Prior Publication Data

US 2011/0296568 P1 Dec. 1, 2011

(51) Int. Cl.
*A01H 5/00* (2006.01)

(52) U.S. Cl. ..... Plt./156

(58) Field of Classification Search ..... Plt./156, Plt./373

See application file for complete search history.

(56) References Cited

U.S. PATENT DOCUMENTS

| | | | |
|---|---|---|---|
| PP8,863 | P | 8/1994 | Oda et al. |
| PP12,861 | P2 | 8/2002 | Loison |
| PP16,328 | P3 | 3/2006 | Morales et al. |
| PP16,396 | P3 | 3/2006 | Gonzales et al. |
| PP20,885 | P3 | 3/2010 | Young et al. |

FOREIGN PATENT DOCUMENTS

| | | |
|---|---|---|
| AU | 2005/353 | 2/2006 |
| AU | 2007/036 | 2/2007 |

OTHER PUBLICATIONS

Clark, J.R. & Finn, C.E., Register of New Fruit and Nut Cultivars List 45, Horticultural Science vol. 45(5) 2010; pp. 740-742.
The Brooks and Olmo Register of Fruit and Varieties, 3rd Ed., ASHS Press 1997; p. 580.

*Primary Examiner* — Wendy C Haas
(74) *Attorney, Agent, or Firm* — Seth M. Reiss, AAL, ALLLC; Seth M. Reiss

(57) ABSTRACT

A new pineapple (*Ananas comosus*) variety of the Bromeliaceae family was developed from a cross between the parental lines 'Dry Sweet'×'Hilo White' and has been designated 'Franklynn'. This new variety differs from its progenitors in having a higher Brix value, distinct fruit skin and flesh colors, and excellent eating quality. The plant is characterized by relatively (for pineapple) flat, spineless leaves that are green with purple coloration, and a peduncle that is partially or completely obscured by a high number of green bracts. The plant has a cylindrical and symmetrical fruit borne on a peduncle. The fruit has a lightly textured shell and flat fruitlets (eyes) with a medium sized crown. When unripe, the fruit shell is greyed-purple (RHS 187A), turning to a greyed-orange color (RHS 167B) when ripe. The fruit flesh appears cream colored and codes to a pale yellow (RHS 8D).

3 Drawing Sheets

Botanical designation: *Ananas comosus*.
Variety denomination: 'Franklynn'.

BACKGROUND AND BRIEF SUMMARY OF THE INVENTION

A new pineapple (*Ananas comosus*) variety of the Bromeliaceae family was developed from a cross between the parental lines 'Dry Sweet' and 'Hilo White' pineapple plant varieties and has been designated 'Franklynn'.

'Franklynn' is a selection from the F1 (first generation) hybrid of 'Dry Sweet' (seed parent, unpatented) and 'Hilo White' (pollen parent, unpatented).

'Hilo White' is a variety of unknown parentage cultivated in Hilo, Hi. having a white, sweet flesh. It is similar in appearance to 'Smooth Cayenne' but is readily distinguished from 'Smooth Cayenne' by a complete absence of spines on the leaves and a white flesh color.

'Dry Sweet' is a mutation of 'Smooth Cayenne' having dry, sweet fruits and a Brix value of 17-19%. The cultural characteristics of 'Dry Sweet' have not been evaluated but they are assumed to be similar to those of 'Smooth Cayenne'.

No record was found that either parent has been used in the production of a hybrid pineapple.

Seeds of the F1 hybrid of 'Dry Sweet'×'Hilo White' were first planted in Waimanalo, Hi. in the 1997. Between the years 2000 and 2002, one plant was selected as being superior on the basis of vigor, fruit size, flavor, sweetness, and flesh texture. This plant was propagated asexually from slips, shoots, or crowns of mature fruits. The new cultivar 'Franklynn' has been asexually propagated from slips, shoots or crowns of mature fruits in Waimanalo, Hi. for multiple generations from 2000 to 2010 and this propagation has demonstrated that the characteristics of the new cultivar are firmly fixed and stably reproduced true-to-type through successive generations.

'Franklynn' is most similar to the commercial variety 'Hilo White' in taste and appearance. However, 'Franklynn' differs from 'Hilo White' in the following manners:

1. 'Franklynn' has dark orange skin on the mature fruit whereas 'Hilo White' has a yellow skin.
2. 'Franklynn' has a shorter peduncle and many more green, leafy bracts on the peduncle than does 'Hilo White'.
3. 'Franklynn' fruit has yellow-white (cream) colored flesh while 'Hilo White' fruit has white flesh.
4. The 'Franklynn' fruit is sweeter than the 'Hilo White' fruit.

'Franklynn' is similar to the variety 'Dry Sweet' in having a similar growth and sweetness. However, 'Franklynn' differs from 'Dry Sweet' in the following manners:

1. The mature fruit of 'Franklynn' has dark orange shell rather than the yellow shell of the fruit of 'Dry Sweet'.
2. The fruit of 'Franklynn' is sweeter than that of 'Dry Sweet', having a Brix value ranging from 21% to 26% while the Brix value of 'Dry Sweet' ranges from 17% to 19%.
3. The fruit of 'Dry Sweet' is more acidic than that of 'Franklynn'.
4. 'Franklynn' has leaf margins that are completely smooth and free of spines while 'Dry Sweet' has spines at the leaf tip margins and occasionally at the leaf base.

BRIEF DESCRIPTION OF THE DRAWINGS

The accompanying drawings serve, by color photographic means, to illustrate the new plant variety through the depiction of typical specimens of the new pineapple variety, as true as reasonably possible.

DETAILED BOTANICAL DESCRIPTION

The following detailed descriptions of the new plant variety are based upon observations of specimens grown in Waimanalo, the island of Oahu, Hi. Color terminology and color designations set forth herein are in accordance with The R.H.S. Colour Chart of The Royal Horticultural Society of London (R.H.S.) (2001).

Name: *Ananas comosus* var. 'Franklynn'.

Parentage:

*III. Seed parent.*—'Dry Sweet'.

*IV. Pollen parent.*—*'Hilo White'.*

Origin: F1 hybrid of 'Dry Sweet' and 'Hilo White'.

Classification:

*III. Botanic.*—Bromeliaceae or pineapple family. Subfamily: Bromeliodeae. Genus: *Ananas*. Species: *comosus*. Var. *comosus;* Cultivar: 'Franklynn'.

*IV. Commercial.*—Bromeliad fruit plant.

Form: Terrestrial (in cultivation) with overlapping sessile leaves that form a funnel-shaped rosette. Once reproductive development has been initiated, either naturally or as a result of treatment with ethylene or ethephon, the composite inflorescence (a sorus) is borne upward through the leaf whorl as the peduncle elongates. The fruit is composed of 50 or more individual fruitlets and fruit size is determined by fruitlet number and average size. The fruitlets are fused together and the aggregate forms the pineapple fruit. The flower is composed of three sepals, three petals, six stamens, and a trilobed style, which is attached to the ovary. Three thick, fleshy sepals and a subtending fleshy bract form the outer covering of each fruitlet and these structures are fused together to form the fruit shell. The inflorescence is a sorus. (FIG. 3) A few to several rootable offshoots (slips) are initiated below the inflorescence during or subsequent to anthesis. Stem offshoots (suckers) form on the main plant stem. These are retained to produce a subsequent crop after the initial fruit harvest or can be harvested and used as planting material. Production of offshoots (suckers, hapas and slips) varies with the size of the plant at fruiting and with season. Slip numbers for 'Franklynn' vary from 1 to 8 per plant, with a mean of 3.9±2.4 (n=10). Plant height at fruiting ranges from 66 to 76 cm and mean plant height is 70.2 cm±4.2 cm. Mean height from the ground to the base of the fruit is 53 cm±4.1 cm.

Stems: Stem is upright, club-shaped and tapering sharply at its base. It is completely sheathed by overlapping leaves arranged in acropetal fashion, and the plant is heart-shaped in cross section. Stem diameter is 6.2 cm to 6.3 cm measured above the tapered base for a 4.4 kg plant.

Figure 1:
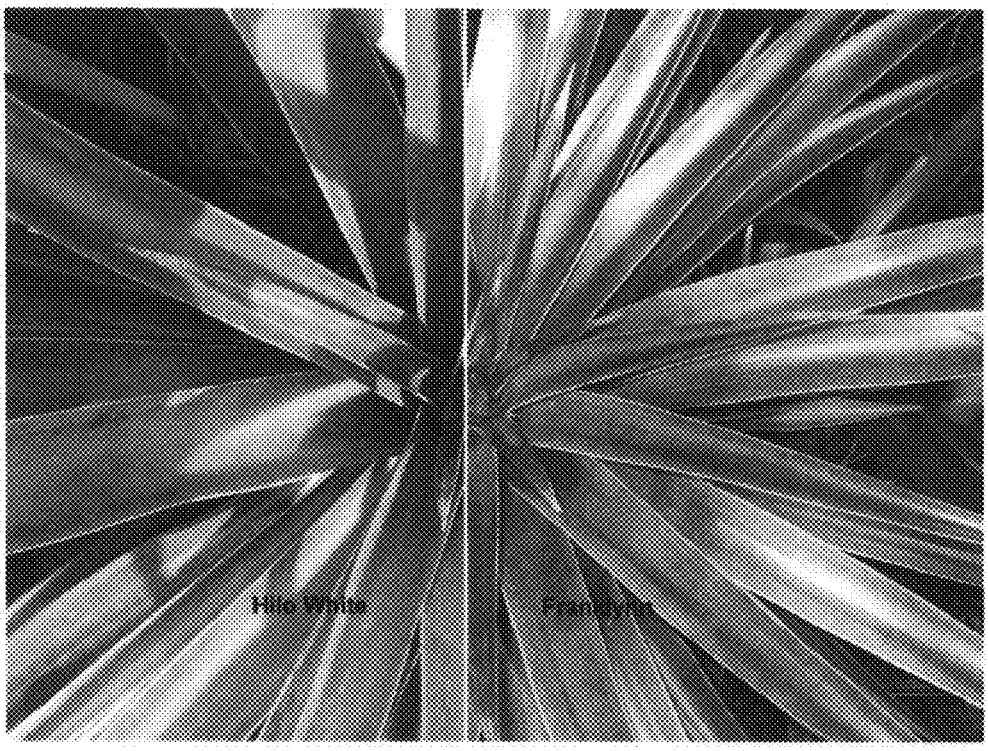
FIG. 1 illustrates a split composite photograph of vegetative plants of typical 'Hilo White' and 'Franklynn' varieties.

Leaves:

*V. General.*—Leaves are sessile, lanceolate in form, elongated and succulent, with acuminate apex shape, and forming a rosette with a 5/13 phyllotaxy. Depending on growing conditions, the number of leaves per plant at the time of forced flower induction may vary from 40 to 60. The breakage resistance of the leaf is low, and foliage attitude is open (Descriptors for Pineapple, IBPGR, Rome 1991). Trichomes cover the abaxial (lower) leaf surface and, less common in commercial pineapple cultivars, also cover the adaxial (upper) side of the leaves, rendering it silvery-white in color. (FIG. 1) (Descriptors for Pineapple, IBPGR, Rome 1991).

*VI. Color.*—The color of the upper surface of the D leaf (youngest physiologically mature leaf) is green (RHS 137B) to grey green (RHS 189A). The pigmented area where anthocyanins are more dominant is greyed purple (RHS 183C).

*VII. Margins.*—The leaves are completely smooth and free of spines. Thickness of the longest leaf ranges from 2.3 cm to 2.7 mm at middle section when the leaf water storage tissue is fully turgid.

Figure 2:
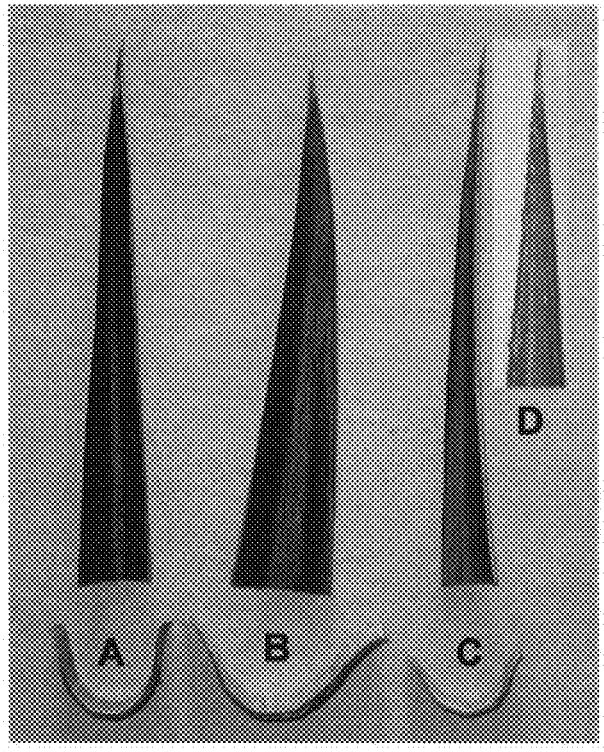
FIG. 2 shows the leaf tips and leaf cross sections at mid-length of 'Hilo White' (A), 'Franklynn' (B), 'Dry Sweet' (C) and enlarged leaf tip of 'Dry Sweet' showing small thorns (D).

*VIII. Leaf size.*—Depending on growing conditions, the length of the D leaf may vary from 63 cm to 84 cm, with a mean of 74.4 cm±7.5 cm. Leaf width at mid-length ranges from 5.25 cm to 5.5 cm, mean of 5.3 cm±2.9 cm. Longitudinal undulations are present across the upper surface of all leaves and the undulations run the entire length of the leaf. Average weight of the 'D' leaf at the time of forced induction ranges from 41 g to 70 g (10 leaves), mean of 51.7 g±9 g. Leaves in cross section form a shallow trough. (FIG. 2).

Figure 3:
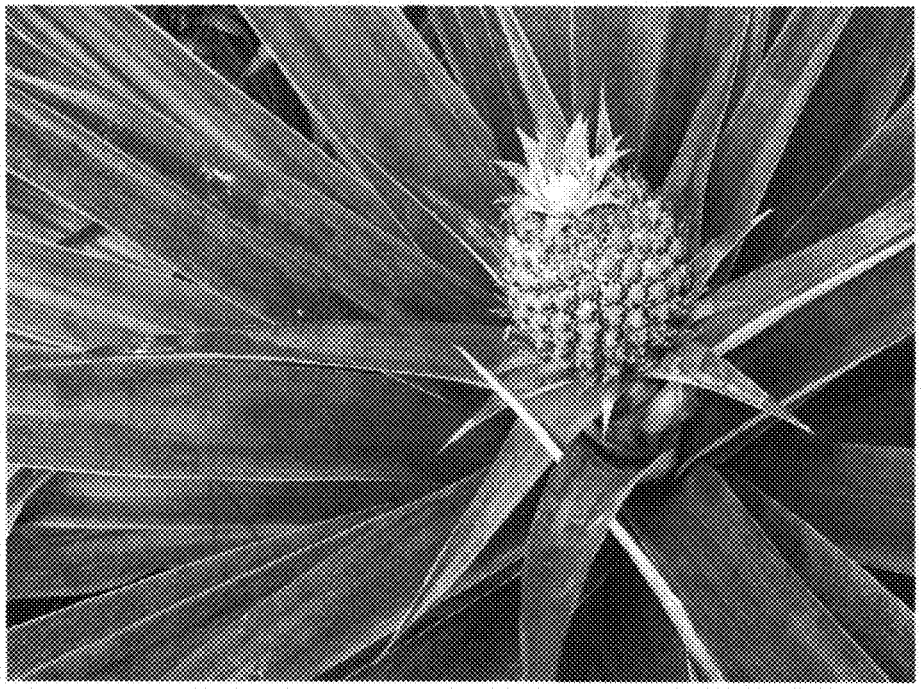
FIG. 3 shows 'Franklynn' inflorescence at early anthesis demonstrating red bracts.

Inflorescence: (FIG. 3).

*IV. General.*—Pineapple inflorescence is a composite (sorus), and each floret has a self-incompatible bisexual flower containing three sepals, six stamens, three stigmas, and three carpels. The inflorescence is borne on a cylindrical peduncle that is obscured by a relatively large number of green, leafy bracts. The mean days from forced reproductive development on Dec. 3, 2009 to opening of the first flower was 91 days±3 days (n=7).

*V. Floral bract.*—The floral bract, which covers approximately ⅓ of the fruitlet, is of aristate apex and truncate base.

*VI. Petals.*—Petals are smooth with an oblong shape and a closed orientation. The petal number is 3. The apex is subacute and the base is truncate. Petal color is red purple (RHS 88A), and the area without color is medium (typical range for pineapple is none, small, medium and large; Descriptors for Pineapple, IBPGR, Rome 1991).

Figure 4:
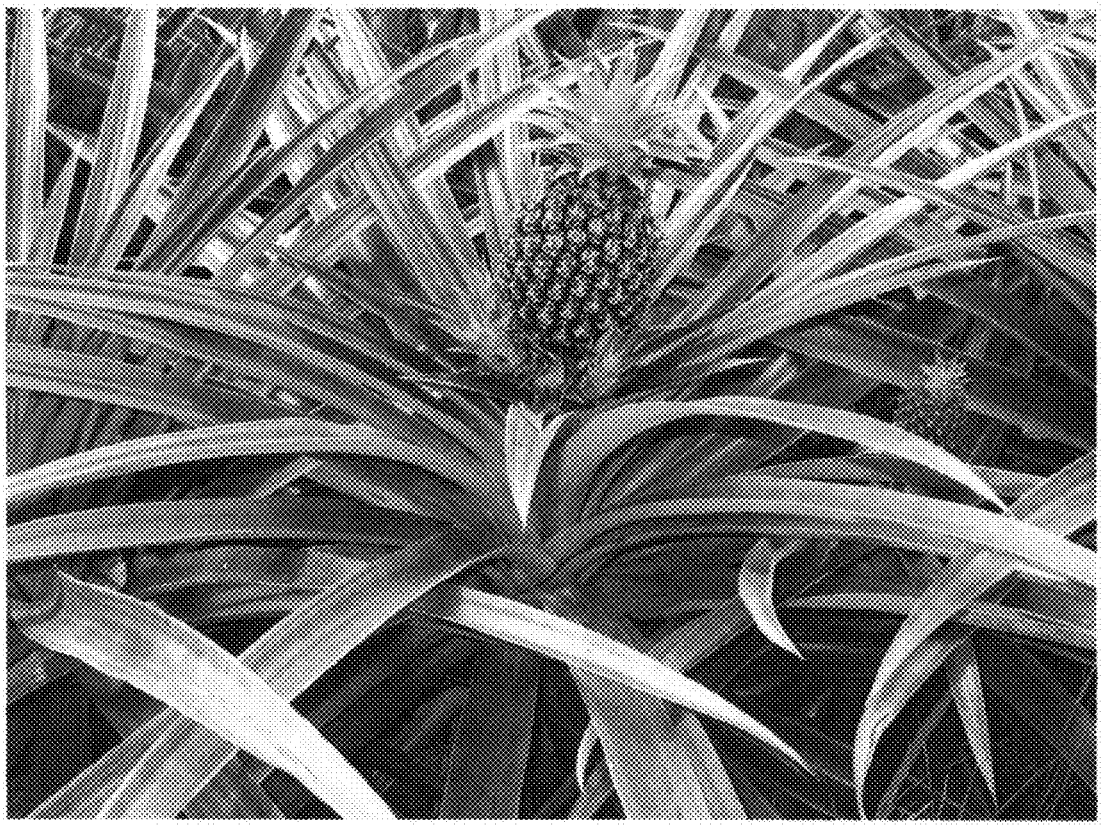
FIG. 4 shows a fruiting 'Franklynn' plant with slips, the peduncle obscured by green, leafy bracts.
Figure 5:
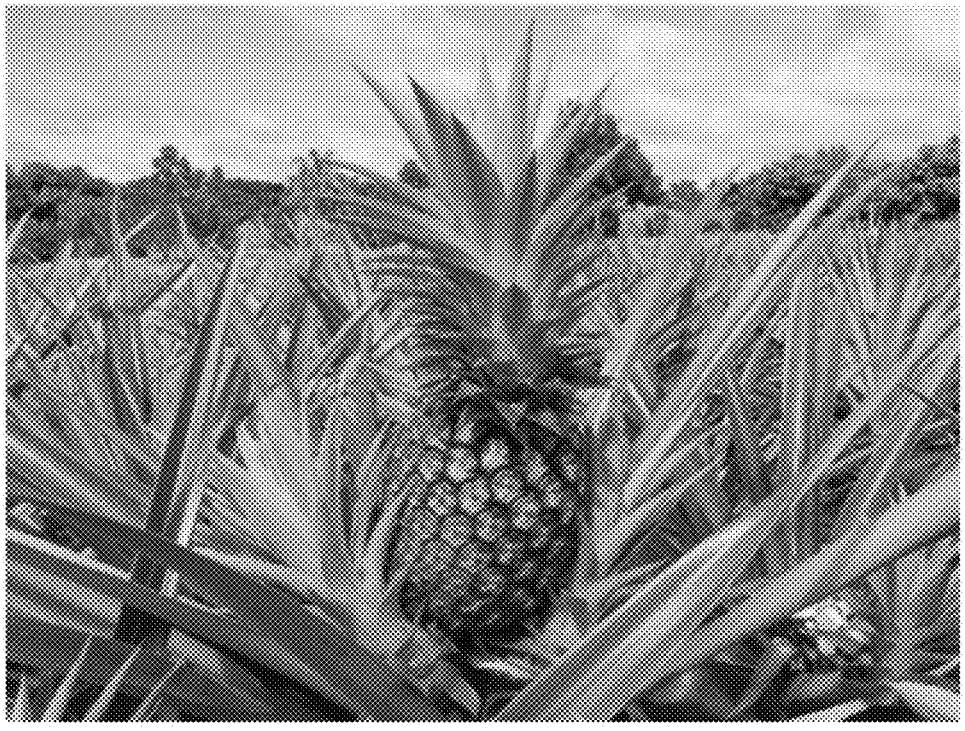
FIG. 5 illustrates the 'Franklynn' hybrid with ripe fruit.
Figure 6:
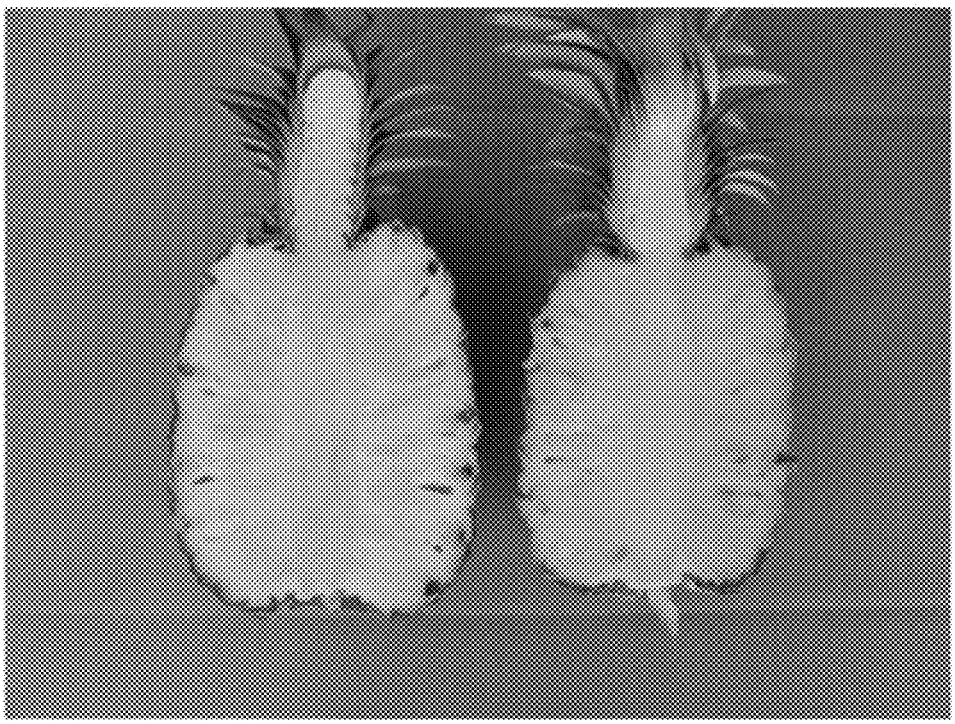
FIG. 6 shows the flesh of the ripe fruit of the 'Franklyn' hybrid (right) compared with the flesh of the ripe fruit of the 'Hilo White' parent (left) in cross-section.

Fruit: (FIG. 4, FIG. 5 and FIG. 6).

*V. Fruit shape and outside color* (*FIG.* 5).—The fruit shape is conical. The number of fruitlets varies with plant size at forced induction of reproductive development and, in plants producing the largest fruits, was 121.3 fruitlets±16.3 fruitlets (n=6) per fruit. The coloration of the fruit shell ranges from greyed-orange (RHS 167B) to greyed-yellow (RHS 162C).

*VI. Fruit dimensions.*—Fruit length is 14.2 cm±1.4 cm; fruit diameter is 12.5 cm±0.8 cm; and fruit weight is 1399 g±249 g. Fruit core diameter is 3.0 cm±0.5 cm. Mean fruitlets per fruit is 112.8 fruitlets±15.6 fruitlets (n=10).

*VII. Crown characteristics.*—Crown length is 21.8 cm±3.4 cm (n=13); crown weight is 305.2 g±119.6 g (n=13).

*VIII. Flesh and juice characteristics at maturity.* (*FIG.* 6 *right side*).—The flesh is compact, fine, smooth-creamy, low in fiber, mildly acidic and very sweet with a pleasant mild aroma. The fruit core is relatively low in fiber and edible. Flesh color is creamy and codes to a pale yellow (RHS 8D). Fruit mean Brix value (TSS) is 22.9±2.5 (n=13); titratable acids 7.7 mg/100 ml juice±0.8 mg/100 ml juice (n=13); ascorbic acid 11.8 mg/100 ml juice±4.5 mg/100 ml juice (n=10), which is a relatively low level typical of 'Smooth Cayenne'; and has a PH range of 4.1 to 4.4, with a mean of 4.29. Fruit translucency is 1.4±0.7 (n=13) on a scale of 1 to 5.

*V. Days to maturity.*—Average days from forcing (winter forcing, duration would be shorter with summer forcing) to flowering is 91 days±3 days (n=7), and from forcing to harvest is 191 days±4 days (n=8).

Peduncle: The colored peduncle bracts have a lanceolate form. The average number of these bracts is 10.5, with a longest bract length of 33 cm. Bract color is deep pink (RHS 46B-C). The peduncle is partially to completely obscured by green, leafy bracts. (FIG. 4) Peduncle length is 20.9 cm±3.7 cm (n=35). Peduncle diameter is 3.04±0.3 cm at middle section.

I claim:

1. A new and distinct variety of pineapple plant designated 'Franklynn' substantially as shown and described herein.

* * * * *